US00PP29655P3

(12) United States Plant Patent
Pan

(10) Patent No.: US PP29,655 P3
(45) Date of Patent: Sep. 11, 2018

(54) ***LANTANA* PLANT NAMED 'LANZ0012'**

(50) Latin Name: *Lantana camara*
Varietal Denomination: LANZ0012

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 378 days.

(21) Appl. No.: 14/757,048

(22) Filed: Nov. 12, 2015

(65) Prior Publication Data

US 2016/0174445 P1 Jun. 16, 2016

Related U.S. Application Data

(60) Provisional application No. 62/090,960, filed on Dec. 12, 2014.

(51) Int. Cl.
*A01H 5/02* (2018.01)

(52) U.S. Cl.
USPC ..... Plt./227
CPC ..... *A01H 5/02* (2013.01)

(58) Field of Classification Search
USPC ..... Plt./227
CPC ..... A01H 5/02
See application file for complete search history.

*Primary Examiner* — Kent L Bell
(74) *Attorney, Agent, or Firm* — Dale Skalla

(57) ABSTRACT

A new *Lantana* plant named 'LANZ0012' particularly distinguished by uniform golden yellow flowers, large inflorescences, green foliage, and vigorous trailing but tight branching plant habit.

1 Drawing Sheet

Latin name of the genus and species of the plant claimed: *Lantana camara.*

Varietal denomination: 'LANZ0012'.

BACKGROUND OF THE NEW PLANT

The present invention comprises a new *Lantana*, botanically known as *Lantana camara*, and hereinafter referred to by the variety name 'LANZ0012'.

'LANZ0012' is a product of a planned breeding program. The new cultivar has uniform golden yellow flowers, large inflorescences, green foliage, and vigorous trailing but tight branching plant habit.

'LANZ0012' originated from an X-ray mutagen treatment from 'Bant Tragol' (U.S. Plant Pat. No. 20,557). The treatment was made in Jan. 10, 2010 in a lab in Andijk, The Netherlands. The mutated young plants were grown in greenhouse in Apr. 15, 2011 in Gilroy, Calif. The 'Bant Tragol' plant has slightly lighter flower color, looser trailing plant habit, and slightly smaller flower size than 'LANZ0012'.

The 'LANZ0012' was grown again in Apr. 10, 2012 in greenhouse in Gilroy, Calif. In the same year, it was also trialed in summer fields in Gilroy, Calif., Grand Rapids, Mich., and Enkhuizen, The Netherlands. The product advancement decision was made in Sep. 25, 2012 after above field trials were completed.

The first act of asexual reproduction of 'LANZ0012' was accomplished when vegetative cuttings were propagated from the initial selection in a greenhouse in Gilroy, Calif., in Apr. 15, 2011.

BRIEF SUMMARY OF INVENTION

Horticultural examination of plants grown from cuttings of the plant initiated on Apr. 15, 2011 in Gilroy, Calif., and continuing thereafter, has demonstrated that the combination of characteristics as herein disclosed for 'LANZ0012' are firmly fixed and are retained through successive generations of asexual reproduction.

'LANZ0012' has not been observed under all possible environmental conditions. The phenotype may vary significantly with variations in environment such as temperature, light intensity, and day length.

A Plant Breeder's Right for this cultivar was not yet applied for. 'LANZ0012' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0012' with colors being as true as possible with an illustration of this type.

Figure 1:
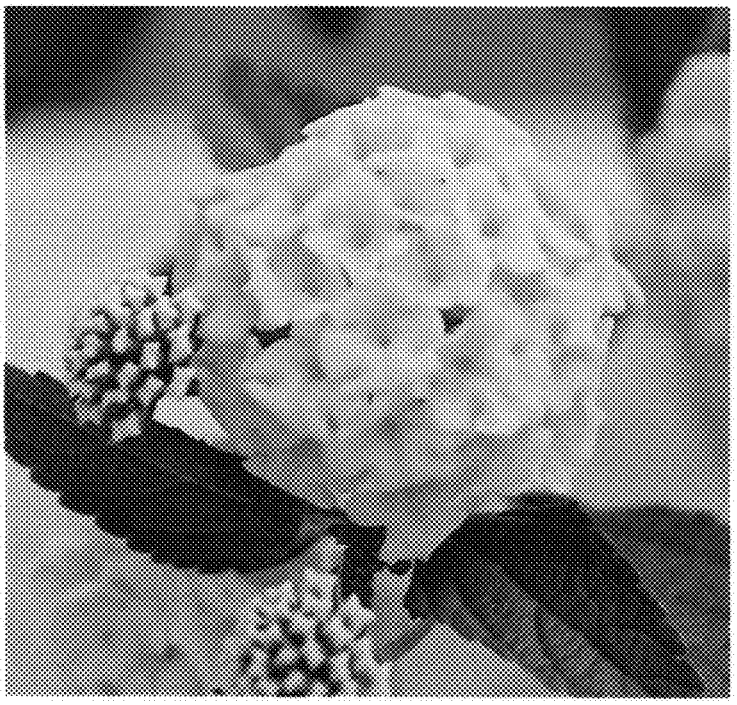
Figure 2:
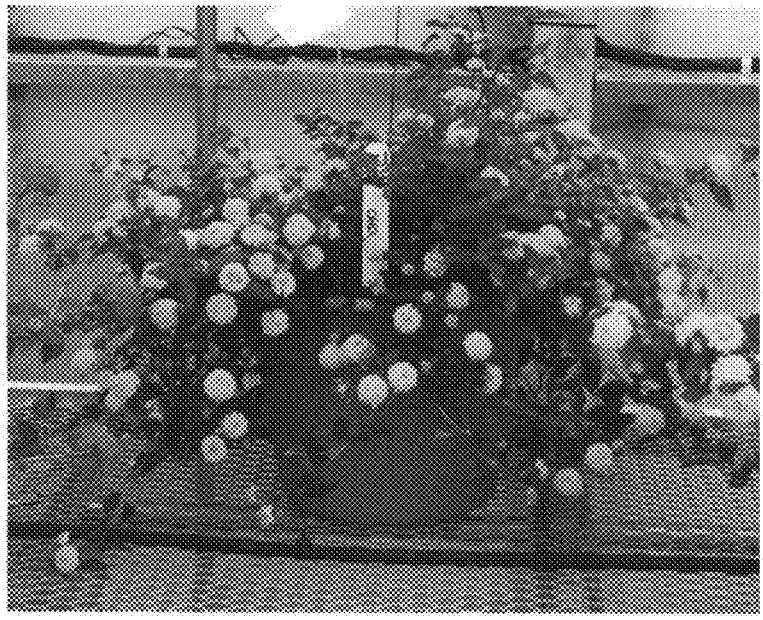

FIG. 1 shows a close-up of an inflorescence and FIG. 2 shows a flowering potted plant of the new variety.

Color references are made to The Royal Horticultural Society Colour Chart (R.H.S.) 2001.

TABLE 1

DIFFERENCES BETWEEN THE NEW VARIETY 'LANZ0012' AND A MOST SIMILAR VARIETY

| | 'LANZ0012' | 'New Gold' (not patented) |
|---|---|---|
| Flower type and color: | Larger flower, deeper colour tone | Slightly smaller flower, and lighter color tone |

TABLE 1-continued

DIFFERENCES BETWEEN THE NEW VARIETY 'LANZ0012' AND A MOST SIMILAR VARIETY

| | 'LANZ0012' | 'New Gold' (not patented) |
|---|---|---|
| Plant habit: | Tighter branching habit | Looser trailing plant habit |
| Plant size: | Vigorous trailing | Vigorous trailing |

DETAILED BOTANICAL DESCRIPTION

The plant descriptions and measurements were taken in Gilroy, Calif. in October 2015. The plants were approximately 28 weeks old and were growing in a 14 inch pot outdoors.

Plant:

*Form, growth and habit.*—Semi-woody, grown as an annual or perennial; Tighter branching habit; vigorous trailing.

*Plant height.*—Approximately 36.5 cm.

*Plant height (inflorescence included).*—Approximately 46.5 cm.

*Plant width.*—Approximately 102 cm.

Foliage:

*Type.*—Opposite.

*Immature, leaf color, upper surface.*—Closest to RHS 137A.

*Lower surface.*—Closest to RHS 147B.

*Mature, leaf color, upper surface.*—Closest to RHS 139A.

*Lower surface.*—Closest to RHS 147B.

*Length.*—4.0-4.5 cm.

*Width.*—1.8-2.3 cm.

*Shape.*—Elliptic.

*Base shape.*—Rounded.

*Apex shape.*—Acute.

*Margin.*—Dentate.

*Texture, upper.*—Hirsute.

*Lower surface.*—Hirsute.

*Pattern of veining.*—Pinnate.

*Petioles color.*—RHS 146C.

*Petioles length.*—0.5-0.7 cm.

*Diameter of petiole.*—0.1-0.2 cm.

*Texture (upper and lower surface).*—Hirsute with some very short glandular hairs.

Stem:

*Color of stem.*—RHB 146C.

*Length of stem.*—20-23.0 cm.

*Diameter.*—0.5 cm.

*Length of internodes.*—2.5-3.0 cm.

*Texture.*—Pilose, hirsute.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—30-33.

*Quantity of inflorescences per plant.*—About 150 (with open florets).

*Lastingness of individual blooms on the plant.*—About 4 weeks (depending on temperatures).

*Fragrance.*—Slightly spicy.

*Umbel horizontal diameter.*—About 3.5 cm.

*Umbel vertical height.*—1.5-2.0 cm.

*Peduncle color.*—RHS 144A.

*Length of peduncle.*—About 2.5 cm.

*Peduncle diameter.*—0.15 cm.

*Texture.*—Hirsute, glandular hairs.

Flower:

*Floret form.*—Corolla salver-shaped to shallow cup-shaped, with a relatively long tube at the base; each flower subtended by a single bract.

*Length of floret.*—1.2-1.5 cm.

*Width of floret.*—0.5-0.8 cm.

*Depth of floret.*—0.5-0.8 cm.

*Young floret, color upper surface.*—RHS 23B to RHS 16C.

*Young floret, color lower surface.*—RHS 16B.

*Mature florets, color upper surface.*—RHS 17A to RHS 23A.

*Mature floret, color lower surface.*—RHS 23A.

*Apex shape.*—Rounded.

*Degree of lobation.*—Moderate.

*Margin.*—Crenate.

*Base.*—Fused.

*Texture, upper surface.*—Papillose.

*Lower surface.*—Papillose.

*Tube, color outer surface.*—Closest to RHS 16B to RHS 145C.

*Tube, color inner surface.*—Closest to RHS 15A.

*Tube, length.*—1.0 cm.

*Tube, diameter (at opening).*—0.15 cm.

*Tube, texture outer surface.*—Pubescent.

*Inner surface.*—Hirsute.

Bud (just before opening):

*Color.*—RHS 23A.

*Length.*—0.4-0.6 cm.

*Width.*—0.2-0.4 cm at the apex.

*Shape.*—Tubular with a flared apex.

Bract:

*Color, upper surface.*—Closest to RHS 147B apex.

*Length.*—0.5-0.6 cm.

*Diameter.*—0.15-0.2 cm.

*Texture, upper surface.*—Hirsute.

*Lower surface.*—Hirsute.

Calyx:

*Number of sepals.*—5, fused sepals forming a short tube around the base of the floret.

*Color of sepals, upper surface.*—RHS 147D.

*Length of sepals.*—0.30 cm.

*Width of sepals.*—0.2 cm.

*Apex shape.*—Acuminate.

*Apex margins.*—Entire.

*Texture, outer surface.*—Pubescent.

*Inner surface.*—Glabrous.

Reproductive organs:

*Gynoecium.*—

*Pistil quantity.*—One.

*Length.*—0.3 cm.

*Style color.*—RHS 174A.

*Style length.*—0.2 cm.

*Stigma color.*—RHS 200A.

*Ovary color.*—RHS 146B.

*Ovary length.*—0.1 cm.

*Ovary diameter.*—0.1 cm

*Androecium.*—

*Stamen quantity.*—4.

*Color of filaments.*—RHS 15A.

*Length filaments.*—0.4-0.5 cm.

*Anther color.*—RHS 200D.

*Length of anthers.*—0.1 cm.

*Color of pollen.*—RHS 200D.

*Pollen amount.*—Normal.

*Fertility/seed set.*—Has not been determined to date.

*Disease/pest resistance.*—Has not been determined to date.

What is claimed is:

1. A new and distinct variety of *Lantana* plant named 'LANZ0012' substantially as illustrated and described herein.

* * * * *